United States Patent
Jackson et al.

(10) Patent No.: US 7,879,358 B2
(45) Date of Patent: Feb. 1, 2011

(54) PULMONARY DELIVERY FOR LEVODOPA

(75) Inventors: Blair Jackson, Quincy, MA (US); David J. Bennett, Brighton, MA (US); Raymond T. Bartus, San Diego, CA (US); Dwaine F. Emerich, Cranston, RI (US)

(73) Assignee: Alkermes, Inc., Waltham, MA (US)

( * ) Notice: Subject to any disclaimer, the term of this patent is extended or adjusted under 35 U.S.C. 154(b) by 2148 days.

(21) Appl. No.: 10/392,342

(22) Filed: Mar. 19, 2003

(65) Prior Publication Data

US 2004/0018989 A1 Jan. 29, 2004

Related U.S. Application Data

(60) Provisional application No. 60/366,471, filed on Mar. 20, 2002.

(51) Int. Cl.
*A61K 9/14* (2006.01)
*A61K 31/26* (2006.01)

(52) U.S. Cl. .................. 424/489; 424/46; 424/488; 514/535

(58) Field of Classification Search .............. 514/567, 514/951, 535; 424/489, 499, 502, 46, 488
See application file for complete search history.

(56) References Cited

U.S. PATENT DOCUMENTS

| | | | |
|---|---|---|---|
| 3,689,643 A | 9/1972 | Plotnikoff | |
| 4,814,161 A | 3/1989 | Jinks et al. | |
| 4,895,719 A | 1/1990 | Radhakrishnan et al. | |
| 5,118,494 A | 6/1992 | Schultz et al. | |
| 5,166,202 A | 11/1992 | Schweizer | |
| 5,284,133 A | 2/1994 | Burns et al. | |
| 5,354,885 A | 10/1994 | Milman et al. | |
| 5,457,100 A | 10/1995 | Daniel | |
| 5,510,350 A | 4/1996 | Oxford et al. | |
| 5,654,007 A | 8/1997 | Johnson et al. | |
| 5,756,071 A | 5/1998 | Mattern et al. | |
| 5,855,913 A | 1/1999 | Hanes et al. | |
| 5,874,064 A | 2/1999 | Edwards et al. | |
| 5,875,776 A | 3/1999 | Vaghefi | |
| 5,922,354 A | 7/1999 | Johnson et al. | |
| 5,981,474 A | 11/1999 | Manning et al. | |
| 5,985,309 A | 11/1999 | Edwards et al. | |
| 6,019,968 A | 2/2000 | Platz et al. | |
| 6,048,857 A | 4/2000 | Ellinwood, Jr. et al. | |
| 6,103,270 A | 8/2000 | Johnson et al. | |
| 6,136,295 A | 10/2000 | Edwards et al. | |
| 6,165,463 A | 12/2000 | Platz et al. | |
| 6,193,954 B1 | 2/2001 | Adjei et al. | |
| 6,461,631 B1 * | 10/2002 | Dunn et al. | ................. 424/426 |
| 6,514,482 B1 | 1/2003 | Bartus et al. | |
| 6,613,308 B2 | 9/2003 | Bartus et al. | |
| 2002/0035993 A1 | 3/2002 | Edwards et al. | |

FOREIGN PATENT DOCUMENTS

| | | |
|---|---|---|
| CA | 2152684 | 6/1995 |
| EP | 0 496 307 A1 | 7/1992 |
| JP | 61022019 A | 1/1986 |
| WO | WO 91/16882 | 11/1991 |
| WO | WO 98/31346 | 7/1998 |
| WO | WO 98/46245 | 10/1998 |
| WO | WO 00/72827 A3 | 12/2000 |
| WO | WO 01/95874 A2 | 12/2001 |

OTHER PUBLICATIONS

Stocchi, F. et al., "The role of l-dopa pharmacodynamic in the pathogenesis of motor fluctuations," *Journal of the Neurological Sciences*, 150(Issue: 1001) Supplement 1, pp. S198 (Sep. 1997). Retrieved Abstract on the Internet [online] [Retrieved on Apr. 5, 2002].

\* cited by examiner

*Primary Examiner*—Johann R Richter
*Assistant Examiner*—Abigail Fisher
(74) *Attorney, Agent, or Firm*—Elmore Patent Law Group, P.C.; Carolyn S. Elmore; Darlene A. Vanstone

(57) ABSTRACT

In one aspect, the invention is related to a method of treating a patient with Parkinson's disease, the method including administering to the respiratory tract of the patient particles that include more than about 90 weight percent (wt %) of levodopa. The particles are delivered to the patient's pulmonary system, preferably to the alveoli or the deep lung.

10 Claims, No Drawings

PULMONARY DELIVERY FOR LEVODOPA

RELATED APPLICATION

This application claims the benefit of U.S. Provisional Application No. 60/366,471, filed Mar. 20, 2002. The entire teachings of the above application are incorporated herein by reference.

BACKGROUND OF THE INVENTION

Parkinson's disease is characterized neuropathologically by degeneration of dopamine neurons in the basal ganglia and neurologically by debilitating tremors, slowness of movement and balance problems. It is estimated that over one million people suffer from Parkinson's disease. Nearly all patients receive the dopamine precursor levodopa or L-Dopa, often in conjunction with the dopa-decarboxylase inhibitor, carbidopa. L-Dopa adequately controls symptoms of Parkinson's disease in the early stages of the disease. However, it tends to become less effective after a period which can vary from several months to several years in the course of the disease.

It is believed that the varying effects of L-Dopa in Parkinson's disease patients are related, at least in part, to the plasma half life of L-Dopa which tends to be very short, in the range of 1 to 3 hours, even when co-administered with carbidopa. In the early stages of the disease, this factor is mitigated by the dopamine storage capacity of the targeted striatal neurons. L-Dopa is taken up and stored by the neurons and is released over time. However, as the disease progresses, dopaminergic neurons degenerate, resulting in decreased dopamine storage capacity. Accordingly, the positive effects of L-Dopa become increasingly related to fluctuations of plasma levels of L-Dopa. In addition, patients tend to develop problems involving gastric emptying and poor intestinal uptake of L-Dopa. Patients exhibit increasingly marked swings in Parkinson's disease symptoms, ranging from a return to classic Parkinson's disease symptoms, when plasma levels fall, to the so-called dyskinesis, when plasma levels temporarily rise too high following L-Dopa administration.

As the disease progresses, conventional L-Dopa therapy involves increasingly frequent, but lower dosing schedules. Many patients, for example, receive L-Dopa every two to three hours. It is found, however, that even frequent doses of L-Dopa are inadequate in controlling Parkinson's disease symptoms. In addition, they inconvenience the patient and often result in non-compliance.

It is also found that even with as many as six to ten L-Dopa doses a day, plasma L-Dopa levels can still fall dangerously low, and the patient can experience very severe Parkinson's disease symptoms. When this happens, additional L-Dopa is administered as intervention therapy to rapidly increase brain dopamine activity. However, orally administered therapy is associated with an onset period of about 30 to 45 minutes during which the patient suffers unnecessarily. In addition, the combined effects of the intervention therapy, with the regularly scheduled dose can lead to overdosing, which can require hospitalization. For example, subcutaneously administered dopamine receptor agonist (apomorphine), often requiring a peripherally acting dopamine antagonist, for example, domperidone, to control dopamine-induced nausea, is inconvenient and invasive.

Therefore, a need exists for methods of treating patients suffering with Parkinson's disease which are at least as effective as conventional therapies yet minimize or eliminate the above-mentioned problems.

SUMMARY OF THE INVENTION

The invention relates to methods of treating disorders of the central nervous system (CNS). More specifically the invention relates to particles and methods for delivering a drug suitable in treating Parkinson's disease, e.g., levodopa, to the pulmonary system.

In one aspect, the invention is related to a method of treating a patient with Parkinson's disease, the method including administering to the respiratory tract of the patient particles that include more than about 90 weight percent (wt %) of levodopa. The particles are delivered to the patient's pulmonary system, preferably to the alveoli region of the deep lung.

In one embodiment of the invention, the particles also include a non-reducing sugar, e.g., trehalose and, optionally, a salt, e.g., sodium chloride (NaCl).

In another embodiment of the invention, the particles also include a phospholipid, e.g., DPPC, or a combination of phospholipids, and optionally a salt, e.g., NaCl.

The invention is also related to a method of preparing spray dried particles that have a high content of L-Dopa, e.g., more than about 90 wt %. The method includes combining L-Dopa, trehalose, NaCl and water to form an aqueous solution and preparing an organic solution (e.g., ethanol), mixing the aqueous solution and organic solution to form a liquid feed mixture and spray drying the liquid feed mixture, thereby forming spray dried particles.

The invention further is related to methods for administering to the pulmonary system a therapeutic dose of L-Dopa in a small number of steps, and preferably in a single, breath activated step. The invention also is related to methods of delivering a therapeutic dose of L-Dopa to the pulmonary system, in a small number of breaths, and preferably in a single breath.

The invention has numerous advantages. The particles of the invention are useful in treating all stages of Parkinson's disease, e.g., ongoing management of the disease, as well as providing rescue therapy. The particles have a high content of L-Dopa and, therefore, the amount of drug that can be contained and administered from a given inhaler capsule is increased, thereby reducing the number of puffs required to deliver a clinically effective dose. The methods of the invention result in forming dry, non-sticky particles in high yields, minimizing material losses and manufacturing costs. The particles have aerodynamic and dispersive properties that render them useful in pulmonary delivery, in particular delivery to the deep lung.

DETAILED DESCRIPTION OF THE INVENTION

The features and other details of the invention, either as steps of the invention or as combination of parts of the invention, will now be more particularly described and pointed out in the claims. It will be understood that the particular embodiments of the invention are shown by way of illustration and not as limitations of the invention. The principle feature of this invention may be employed in various embodiments without departing from the scope of the invention.

The invention is generally related to methods of treating Parkinson's disease. The methods and particles disclosed herein can be used in the ongoing (non-rescue) treatment of Parkinson's disease or during the late stages of the disease, when the methods described herein are particularly well suited to provide rescue therapy. As used herein, "rescue therapy" means on demand, rapid delivery of a drug to a patient to help reduce or control disease symptoms.

Compounds used for treating Parkinson's disease include levodopa (L-Dopa) and carbidopa.

The structure of Carbidopa is shown below:

$C_{10}H_{14}N_2O_4$

The structure of Levodopa is shown below:

$C_9H_{11}NO_4$

Other drugs generally administered in the treatment of Parkinson's disease and which may be suitable in the methods of the invention include, for example, ethosuximide, dopamine agonists such as, but not limited to carbidopa, apomorphine, sopinirole, pramipexole, pergoline, bronaocriptine, and ropinirole. The L-Dopa or other dopamine precursor or agonist may be any form or derivative that is biologically active in the patient being treated. Combinations of drugs also can be employed.

In one embodiment of the invention the particles consist include L-Dopa or other dopamine precursor or agonist as described above. Particularly preferred are particles that include more than about 90 weight percent (wt %), for instance, at least 93 wt % L-Dopa. In one embodiment, the particles include at least 95 wt % L-Dopa. In other embodiments, the presence of a non-reducing sugar or the presence of a salt, as will be described herein, facilitates a lower L-Dopa wt % while maintaining favorable features. The wt % of L-Dopa can be lower to about 75 wt %, or to about 50 wt %, or to about 20 wt %.

In further embodiments, the particles of the invention can also include one or more additional component(s), generally in an amount that is less than 10 weight percent.

In one embodiment the additional component is a non-reducing sugar, for example, but not limited to, trehalose, sucrose, fructose. Trehalose is preferred. Combinations of non-reducing sugars also can be employed. The amount of non-reducing sugar(s), e.g., trehalose, present in the particles of the invention generally is less than 10 wt %, for example, but not limited to, less than 8 wt %, or less than 6 wt %.

Without wishing to be held to a particular interpretation of the invention, it is believed that non-reducing sugars enhance the stability of a drug, such as L-Dopa, that has chemical groups, e.g., amine group, that can potentially react with a sugar that is reducing, e.g., lactose. It is further believed the presence of non-reducing sugars rather than reducing sugars also can benefit compositions that include other bioactive agents or drugs, such as, for example, Carbidopa, epinephrine and other catecholamines.

In another embodiment, the particles of the invention include, in addition to L-Dopa, one or more phospholipids. Specific examples of phospholipids include but are not limited to phosphatidylcholines dipalmitoyl phosphatidylcholine (DPPC), dipalmitoyl phosphatidylethanolamine (DPPE), distearoyl phosphatidylcholine (DSPC), dipalmitoyl phosphatidyl glycerol (DPPG) or any combination thereof. The amount of phospholipids, e.g., DPPC, present in the particles of the invention generally is less than 10 wt %.

The phospholipids or combinations thereof and methods of preparing particles having desired release properties are described in U.S. application Ser. No. 09/792,869 entitled "Modulation of Release from Dry Powder Formulations", filed on Feb. 23, 2001, which is a continuation-in-part of U.S. application Ser. No. 09/644,736 entitled "Modulation of Release from Dry Powder Formulations", filed on Aug. 23, 2000, both of which claim the benefit of U.S. Provisional Patent Application No. 60/150,742 entitled "Modulation of Release From Dry Powder Formulations by Controlling Matrix Transition", filed on Aug. 25, 1999. The contents of all three applications are incorporated herein by reference in their entirety.

Optionally, the particles include, in addition to a non-reducing sugar(s) or phospholipid(s), a small amount of a strong electrolyte salt, such as, but not limited to, sodium chloride (NaCl). Other salts that can be employed include sodium phosphate, sodium fluoride, sodium sulfate and calcium carbonate. Generally, the amount of salt present in the particles is less than 10 wt %, for example, less than 5 wt %.

Particles that comprise, by weight, greater than 90% of an agent, e.g., L-Dopa, can have local areas of charges on the surface of the particles. This electrostatic charge on the surface of the particles causes the particles to behave in undesirable ways. For example, the presence of the electrostatic charge will cause the particles to stick to the walls of the spray drying chamber, or to the pipe leading from the spray dryer, or to stick within the baghouse, thereby, significantly reducing the percent yield obtained. Additionally, the electrostatic charge can tend to cause the particles to agglomerate when placed in a capsule based system. Dispersing these agglomerates can be difficult and that can manifest itself by either poor emitted doses, poor fine particle fractions, or both. Moreover, particle packing can also be affected by the presence of an electrostatic charge. Particles with like charges in close proximity will repel each other, leaving void spaces in the powder bed. This results in a given mass of particles with an electrostatic charge taking up more space than a given mass of the same powder without an electrostatic charge. Consequently, this limits the upper dose that can be delivered in a single receptacle.

Without wishing to be held to a particular interpretation of the invention, it is believed that a salt, such as NaCl, provides a source of mobile counter-ions. It is believed that the addition of a small salt to particles that have local areas of charge on their surface will reduce the amount of static present in the final powder by providing a source of mobile counter-ions that would associate with the charged regions on the surface. Thereby the yield of the powder produced is improved by reducing powder agglomeration, improving the Fine Particle Fraction (FPF) and emitted dose of the particles and allowing for a larger mass of particles to be packed into a single receptacle. As seen in Table 1, particles comprising L-Dopa and either trehalose or DPPC, with the addition of sodium chloride, show an increased yield of approximately 50-60 fold.

TABLE 1

| Formulation | Ratio | Yield |
|---|---|---|
| L-Dopa/Trehalose | 95/5 | <1% |
| L-Dopa/Trehalose/NaCl | 93/5/2 | 50% |
| L-Dopa/DPPC | 95/5 | <1% |
| L-Dopa/DPPC/NaCl | 90/8/2 | 62% |

Table 2 depicts the effects of sodium chloride on the fine particle fraction and emitted dose of particles comprising L-Dopa and either trehalose or DPPC.

TABLE 2

| Formulation | Ratio | FPF < 5.6 | FPF < 3.4 |
|---|---|---|---|
| L-Dopa/Trehalose | 95/5 | 33 | 12 |
| L-Dopa/Trehalose/NaCl | 93/5/2 | 59 | 40 |
| L-Dopa/DPPC | 95/5 | 29 | 10 |
| L-Dopa/DPPC/NaCl | 90/8/2 | 70 | 54 |

It is believed that the salt effect described above also benefits compositions that include bioactive agents other than L-Dopa. Examples of such active agents include, but are not limited to, Carbidopa, epinephrine, other catecholamines, albuterol, salmeterol, ropinirole and piroxican. Furthermore, compositions that include 90% or less of a bioactive agent, e.g., L-Dopa, also can benefit from adding a salt such as described above.

The particles of the invention can include a surfactant. As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to microparticles, they tend to present moieties to the external environment that do not attract similarly-coated particles, thus reducing particle agglomeration. Surfactants may also promote absorption of a therapeutic or diagnostic agent and increase bioavailability of the agent.

Suitable surfactants which can be employed in fabricating the particles of the invention include but are not limited to Tween-20; Tween-80; hexadecanol; fatty alcohols such as polyethylene glycol (PEG); polyoxyethylene-9-lauryl ether; a surface active fatty acid such as palmitic acid or oleic acid; glycocholate; surfactin; a poloxamer; a sorbitan fatty acid ester such as sorbitan trioleate (Span 85); and tyloxapol.

Other materials which promote fast release kinetics of the medicament can also be employed. For example, biocompatible, and preferably biodegradable polymers can be employed. Particles including such polymeric materials are described in U.S. Pat. No. 5,874,064, issued on Feb. 23, 1999 to Edwards et al., the teachings of which are incorporated herein by reference in their entirety.

The particles can also include a material such as, for example, dextran, polysaccharides, lactose, cyclodextrins, proteins, peptides, polypeptides, amino acids, fatty acids, inorganic compounds, phosphates.

Particles of the invention are suitable for delivering L-Dopa to the pulmonary system. Particles administered to the respiratory tract travel through the upper airways (oropharynx and larynx), the lower airways which include the trachea followed by bifurcations into the bronchi and bronchioli and through the terminal bronchioli which in turn divide into respiratory bronchioli leading then to the ultimate respiratory zone, the alveoli or the deep lung. The particles can be engineered such that most of the mass of particles deposits in the deep lung or alveoli.

The particles of the invention can be administered as part of a pharmaceutical formulation or in combination with other therapies be they oral, pulmonary, by injection or other mode of administration. As described herein, particularly useful pulmonary formulations are spray dried particles having physical characteristics which favor target lung deposition and are formulated to optimize release and bioavailability profiles.

The particles of the invention can be employed in compositions suitable for drug delivery to the pulmonary system. For example, such compositions can include the particles and a pharmaceutically acceptable carrier for administration to a patient, preferably for administration via inhalation.

The particles of the invention are useful for delivery of L-Dopa to the pulmonary system, in particular to the deep lung. The particles are in the form of a dry powder and are characterized by a fine particle fraction (FPF), geometric and aerodynamic dimensions and by other properties, as further described below.

Gravimetric analysis, using Cascade impactors, is a method of measuring the size distribution of airborne particles. The Andersen Cascade Impactor (ACI) is an eight-stage impactor that can separate aerosols into nine distinct fractions based on aerodynamic size. The size cutoffs of each stage are dependent upon the flow rate at which the ACI is operated. Preferably the ACI is calibrated at 60 L/min. In one embodiment, a two-stage collapsed ACI is used for particle optimization. The two-stage collapsed ACI consists of stages 0, 2 and F of the eight-stage ACI and allows for the collection of two separate powder fractions. At each stage an aerosol stream passes through the nozzles and impinges upon the surface. Particles in the aerosol stream with a large enough inertia will impact upon the plate. Smaller particles that do not have enough inertia to impact on the plate will remain in the aerosol stream and be carried to the next stage.

The ACI is calibrated so that the fraction of powder that is collected on a first stage is referred to as fine particle fraction FPF (5.6). This FPF corresponds to the % of particles that have an aerodynamic diameter of less than 5.6 µm. The fraction of powder that passed the first stage of the ACI and is deposited on the collection filter is referred to as FPF(3.4). This corresponds to the % of particles having an aerodynamic diameter of less than 3.4 µm.

The FPF (5.6) fraction has been demonstrated to correlate to the fraction of the powder that is deposited in the lungs of the patient, while the FPF(3.4) has been demonstrated to correlate to the fraction of the powder that reaches the deep lung of a patient.

The FPF of at least 50% of the particles of the invention is less than about 5.6 µm. For example, but not limited to, the FPF of at least 60%, or 70%, or 80%, or 90% of the particles is less than about 5.6 µm.

Another method for measuring the size distribution of airborne particles is the multi-stage liquid impinger (MSLI). The Multi-stage liquid Impinger (MSLI) operates on the same principles as the Anderson Cascade Impactor (ACI), but instead of eight stages there are five in the MSLI. Additionally, instead of each stage consisting of a solid plate, each MSLI stage consists of an methanol-wetted glass frit. The wetted stage is used to prevent bouncing and re-entrainment, which can occur using the ACI. The MSLI is used to provide an indication of the flow rate dependence of the powder. This can be accomplished by operating the MSLI at 30, 60, and 90 L/min and measuring the fraction of the powder collected on stage 1 and the collection filter. If the fractions on each stage remain relatively constant across the different flow rates then the powder is considered to be approaching flow rate independence.

The particles of the invention have a tap density of less than about 0.4 g/cm³. Particles which have a tap density of less than about 0.4 g/cm³ are referred to herein as "aerodynamically light particles". For example, the particles have a tap density less than about 0.3 g/cm³, or a tap density less than about 0.2 g/cm³, a tap density less than about 0.1 g/cm³. Tap density can be measured by using instruments known to those skilled in the art such as the Dual Platform Microprocessor Controlled Tap Density Tester (Vankel, N.C.) or a Geopyc™ instrument (Micrometrics Instrument Corp., Norcross, Ga. 30093). Tap density is a standard measure of the envelope mass density. Tap density can be determined using the method of USP Bulk Density and Tapped Density, United States Pharmacopia convention, Rockville, Md., 10$^{th}$ Supplement, 4950-4951, 1999. Features which can contribute to low tap density include irregular surface texture and porous structure.

The envelope mass density of an isotropic particle is defined as the mass of the particle divided by the minimum sphere envelope volume within which it can be enclosed. In one embodiment of the invention, the particles have an envelope mass density of less than about 0.4 g/cm³.

The particles of the invention have a preferred size, e.g., a volume median geometric diameter (VMGD) of at least about 1 micron (μm). In one embodiment, the VMGD is from about 1 μm to 30 μm, or any subrange encompassed by about 1 μm to 30 μm, for example, but not limited to, from about 5 μm to about 30 μm, or from about 10 μm to 30 μm. For example, the particles have a VMGD ranging from about 1 μm to 10 μm, or from about 3 μm to 7 μm, or from about 5 μm to 15 μm or from about 9 μm to about 30 μm. The particles have a median diameter, mass median diameter (MMD), a mass median envelope diameter (MMED) or a mass median geometric diameter (MMGD) of at least 1 μm, for example, 5 μm or near to or greater than about 10 μm. For example, the particles have a MMGD greater than about 1 μm and ranging to about 30 μm, or any subrange encompassed by about 1 μm to 30 μm, for example, but not limited to, from about 5 μm to 30 μm or from about 10 μm to about 30 μm.

The diameter of the spray-dried particles, for example, the VMGD, can be measured using a laser diffraction instrument (for example Helos, manufactured by Sympatec, Princeton, N.J.). Other instruments for measuring particle diameter are well know in the art. The diameter of particles in a sample will range depending upon factors such as particle composition and methods of synthesis. The distribution of size of particles in a sample can be selected to permit optimal deposition to targeted sites within the respiratory tract.

Aerodynamically light particles preferably have "mass median aerodynamic diameter" (MMAD), also referred to herein as "aerodynamic diameter", between about 1 μm and about 5 μm or any subrange encompassed between about 1 μm and about 5 μm. For example, but not limited to, the MMAD is between about 1 μm and about 3 μm, or the MMAD is between about 3 μm and about 5 μm.

Experimentally, aerodynamic diameter can be determined by employing a gravitational settling method, whereby the time for an ensemble of particles to settle a certain distance is used to infer directly the aerodynamic diameter of the particles. An indirect method for measuring the mass median aerodynamic diameter (MMAD) is the multi-stage liquid impinger (MSLI).

The aerodynamic diameter, $d_{aer}$, can be calculated from the equation:

$$d_{aer} = d_g\sqrt{\rho_{tap}}$$

where $d_g$ is the geometric diameter, for example the MMGD, and $\rho$ is the powder density.

Particles which have a tap density less than about 0.4 g/cm³, median diameters of at least about 1 μm, for eample, at least about 5 μm, and an aerodynamic diameter of between about 1 μm and about 5 μm, preferably between about 1 μm and about 3 μm, are more capable of escaping inertial and gravitational deposition in the oropharyngeal region, and are targeted to the airways, particularly the deep lung. The use of larger, more porous particles is advantageous since they are able to aerosolize more efficiently than smaller, denser aerosol particles such as those currently used for inhalation therapies.

In comparison to smaller, relatively denser particles the larger aerodynamically light particles, preferably having a median diameter of at least about 5 μm, also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond about 3 μm. Kawaguchi, H., et al., *Biomaterials*, 7: 61-66 (1986); Krenis, L. J. and Strauss, B., *Proc. Soc. Exp. Med.*, 107: 748-750 (1961); and Rudt, S. and Muller, R. H., *J. Contr. Rel.*, 22: 263-272 (1992). For particles of statistically isotropic shape, such as spheres with rough surfaces, the particle envelope volume is approximately equivalent to the volume of cytosolic space required within a macrophage for complete particle phagocytosis.

The particles may be fabricated with the appropriate material, surface roughness, diameter and tap density for localized delivery to selected regions of the respiratory tract such as the deep lung or upper or central airways. For example, higher density or larger particles may be used for upper airway delivery, or a mixture of varying sized particles in a sample, provided with the same or different therapeutic agent may be administered to target different regions of the lung in one administration. Particles having an aerodynamic diameter ranging from about 3 to about 5 μm are preferred for delivery to the central and upper airways. Particles having and aerodynamic diameter ranging from about 1 to about 3 μm are preferred for delivery to the deep lung.

Inertial impaction and gravitational settling of aerosols are predominant deposition mechanisms in the airways and acini of the lungs during normal breathing conditions. Edwards, D. A., *J. Aerosol Sci.*, 26: 293-317 (1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 μm), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, d (Gonda, I., "Physico-chemical principles in aerosol delivery," in *Topics in Pharmaceutical Sciences* 1991 (eds. D. J. A. Crommelin and K. K. Midha), pp. 95-117, Stuttgart: Medpharm Scientific Publishers, 1992)), by the formula:

$$d_{aer} = d\sqrt{\rho}$$

where the envelope mass ρ is in units of g/cm³. Maximal deposition of monodispersed aerosol particles in the alveolar region of the human lung (~60%) occurs for an aerodynamic diameter of approximately $d_{aer}=3$ μm. Heyder, J. et al., *J. Aerosol Sci.*, 17: 811-825 (1986). Due to their small envelope mass density, the actual diameter d of aerodynamically light particles comprising a monodisperse inhaled powder that will exhibit maximum deep-lung deposition is:

$$d=3/\sqrt{\rho} \mu m \text{ (where } \rho<1 \text{ g/cm}^3\text{);}$$

where d is always greater than 3 μm. For example, aerodynamically light particles that display an envelope mass density, $\rho=0.1$ g/cm$^3$, will exhibit a maximum deposition for particles having envelope diameters as large as 9.5 μm. The increased particle size diminishes interparticle adhesion forces. Visser, J., *Powder Technology*, 58: 1-10. Thus, large particle size increases efficiency of aerosolization to the deep lung for particles of low envelope mass density, in addition to contributing to lower phagocytic losses.

The aerodynamic diameter can be calculated to provide for maximum deposition within the lungs. Previously this was achieved by the use of very small particles of less than about five microns in diameter, preferably between about one and about three microns, which are then subject to phagocytosis. Selection of particles which have a larger diameter, but which are sufficiently light (hence the characterization "aerodynamically light"), results in an equivalent delivery to the lungs, but the larger size particles are not phagocytosed. Improved delivery can be obtained by using particles with a rough or uneven surface relative to those with a smooth surface.

In another embodiment of the invention, the particles have an envelope mass density, also referred to herein as "mass density" of less than about 0.4 g/cm$^3$. Mass density and the relationship between mass density, mean diameter and aerodynamic diameter are discussed in U.S. Pat. No. 6,254,854, issued on Jul. 3, 2001, to Edwards, et al., which is incorporated herein by reference in its entirety.

The invention also is related to producing particles that have compositions and aerodynamic properties described above. The method includes spray drying. Generally, spray-drying techniques are described, for example, by K. Masters in "Spray Drying Handbook", John Wiley & Sons, New York, 1984.

The present invention is related to a method for preparing a dry powder composition. In this method, first and second components are prepared, one of which comprises an active agent. For example, the first component comprises an active agent dissolved in an aqueous solvent, and the second component comprises an excipient dissolved in an organic solvent. The first and second components are combined either directly or through a static mixer to form a combination. The first and second components are such that combining them causes degradation in one of the components. For example, the active agent is incompatible with the other component. In such a method, the incompatible active agent is added last. The combination is atomized to produce droplets that are dried to form dry particles. In one aspect of this method, the atomizing step is performed immediately after the components are combined in the static mixer.

Suitable organic solvents that can be present in the mixture being spray dried include, but are not limited to, alcohols for example, ethanol, methanol, propanol, isopropanol, butanols, and others. Other organic solvents include, but are not limited to, perfluorocarbons, dichloromethane, chloroform, ether, ethyl acetate, methyl tert-butyl ether and others. Aqueous solvents that can be present in the feed mixture include water and buffered solutions. Both organic and aqueous solvents can be present in the spray-drying mixture fed to the spray dryer. In one embodiment, an ethanol/water solvent is preferred with the ethanol:water ratio ranging from about 20:80 to about 80:20. The mixture can have an acidic or alkaline pH. Optionally, a pH buffer can be included. Preferably, the pH can range from about 3 to about 10, for example, from about 6 to about 8.

A method for preparing a dry powder composition is provided. In such a method, a first phase is prepared that comprises L-Dopa and trehalose and optionally salts. A second phase is prepared that comprises ethanol. The first and second phases are combined in a static mixer to form a combination. The combination is atomized to produce droplets that are dried to form dry particles. In an Alternative, only the first phase is prepared and atomized to produce droplets that are dried to form dry particles.

A method for preparing a dry powder composition is provided. In such a method, a first phase is prepared that comprises L-Dopa and optionally salts. A second phase is prepared that comprises DPPC in ethanol. The first and second phases are combined in a static mixer to form a combination. The combination is atomized to produce droplets that are dried to form dry particles.

An apparatus for preparing a dry powder composition is provided. The apparatus includes a static mixer (e.g., a static mixer as more fully described in U.S. Pat. No. 4,511,258, the entirety of which is incorporated herein by reference, or other suitable static mixers such as, but not limited to, model 1/4-21, made by Koflo Corporation.) having an inlet end and an outlet end. The static mixer is operative to combine an aqueous component with an organic component to form a combination. Means are provided for transporting the aqueous component and the organic component to the inlet end of the static mixer. An atomizer is in fluid communication with the outlet end of the static mixer to atomize the combination into droplets. The droplets are dried in a dryer to form dry particles. The atomizer can be a rotary atomizer. Such a rotary atomizer may be vaneless, or may contain a plurality of vanes. Alternatively, the atomizer can be a two-fluid mixing nozzle. Such a two-fluid mixing nozzle may be an internal mixing nozzle or an external mixing nozzle. The means for transporting the aqueous and organic components can be two separate pumps, or a single pump. The aqueous and organic components are transported to the static mixer at substantially the same rate. The apparatus can also include a geometric particle sizer that determines a geometric diameter of the dry particles, and an aerodynamic particle sizer that determines an aerodynamic diameter of the dry particles.

The aqueous solvent and the organic solvent that make up the L-Dopa solution are combined either directly or through a static mixer. The L-Dopa solution is then transferred to the rotary atomizer (aka spray dryer) at a flow rate of about 5 to 28 g/min (mass) and about 6 to 80 ml/min (volumetric). For example, the L-Dopa solution is transferred to the spray drier at a flow rate of 30 g/min and 31 ml/min. The 2-fluid nozzle disperses the liquid solution into a spray of fine droplets which come into contact with a heated drying air or heated drying gas (e.g., Nitrogen) under the following conditions:

The pressure within the nozzle is from about 10 psi to 100 psi; the heated air or gas has a feed rate of about 80 to 110 kg/hr and an atomization flow rate of about 13 to 67 g/min (mass) and a liquid feed of 10 to 70 ml/min (volumetric); a gas to liquid ratio from about 1:3 to 6:1; an inlet temperature from about 90° C. to 150° C.; an outlet temperature from about 40° C. to 71° C.; a baghouse outlet temperature from about 42° C. to 55° C. For example, but not limited to, the pressure within the nozzle is set at 75 psi; the heated gas has a feed rate of 95 kg/hr; and an atomizer gas flow rate of 22.5 g/min and a liquid feed rate of 70 ml/min; the gas to liquid ratio is 1:3; the inlet temperature is 121° C.; the outlet temperature is 48° C.; the baghouse temperature is 43° C.

The contact between the heated nitrogen and the liquid droplets causes the liquid to evaporate and porous particles to result. The resulting gas-solid stream is fed to the product filter, which retains the fine solid particles and allows that hot gas stream, containing the drying gas, evaporated water and ethanol, to pass. The formulation and spray drying parameters are manipulated to obtain particles with desirable physical and chemical characteristics. Other spray-drying techniques are well known to those skilled in the art. An example of a suitable spray dryer using rotary atomization includes the Mobile Niro spray dryer, manufactured by Niro, Denmark. The hot gas can be, for example, air, nitrogen, carbon dioxide or argon.

The particles of the invention are obtained by spray drying using an inlet temperature between about 90° C. and about 150° C. and an outlet temperature between about 40° C. and about 70° C.

The particles can be fabricated with a rough surface texture to reduce particle agglomeration and improve flowability of the powder. The spray-dried particles have improved aerosolization properties. The spray-dried particle can be fabricated with features which enhance aerosolization via dry powder inhaler devices, and lead to lower deposition in the mouth, throat and inhaler device.

Methods and apparatus suitable for forming particles of the present invention are described in U.S. patent application Ser. No. 10/391,199 entitled "Method and Apparatus for Producing Dry Particles", filed concurrently herewith, which is a Continuation-in-part of U.S. patent application Ser. No. 10/101,563 entitled "Method and Apparatus for Producing Dry Particles", filed on Mar. 20, 2002. Methods and apparatus suitable for forming particles of the present invention are described in PCT Patent Application PCT/US03/08398 entitled "Method and Apparatus for Producing Dry Particles", filed concurrently herewith. The entire contents of these applications are incorporated by reference herein.

Administration of particles to the respiratory system can be by means such as known in the art. For example, particles are delivered from an inhalation device such as a dry powder inhaler (DPI). Metered-dose-inhalers (MDI), nebulizers or instillation techniques also can be employed.

Various suitable devices and methods of inhalation which can be used to administer particles to a patient's respiratory tract are known in the art. For example, suitable inhalers are described in U.S. Pat. No. 4,069,819, issued Aug. 5, 1976 to Valentini, et al., U.S. Pat. No. 4,995,385 issued Feb. 26, 1991 to Valentini, et al., and U.S. Pat. No. 5,997,848 issued Dec. 7, 1999 to Patton, et al. Other examples include, but are not limited to, the Spinhaler® (Fisons, Loughborough, U.K.), Rotahaler® (Glaxo-Wellcome, Research Triangle Technology Park, N.C.), FlowCaps® (Hovione, Loures, Portugal), Inhalator® (Boehringer-Ingelheim, Germany), and the Aerolizer® (Novartis, Switzerland), the diskhaler (Glaxo-Wellcome, RTP, N.C.) and others, such as known to those skilled in the art. In one embodiment, the inhaler employed is described in U.S. patent application Ser. No. 09/835,302, entitled "Inhalation Device and Method", by David A. Edwards, et al., filed on Apr. 16, 2001 and in U.S. patent application Ser. No. 10/268,059, entitled "Inhalation Device and Method", by David A. Edwards, et al., filed on Oct. 10, 2002. The entire contents of these applications are incorporated by reference herein.

Delivery to the pulmonary system of particles is by the methods described in U.S. Patent Application, "High Efficient Delivery of a Large Therapeutic Mass Aerosol", application Ser. No. 09/591,307, filed Jun. 9, 2000, and U.S. patent application, "Highly Efficient Delivery of A Large Therapeutic Mass Aerosol", application Ser. No. 09/878,146, filed Jun. 8, 2001. The entire contents of both these applications are incorporated herein by reference. As disclosed therein, particles are held, contained, stored or enclosed in a receptacle. The receptacle, e.g. capsule or blister, has a volume of at least about 0.37 $cm^3$ and can have a design suitable for use in a dry powder inhaler. Larger receptacles having a volume of at least about 0.48 $cm^3$, 0.67 $cm^3$ or 0.95 $cm^3$ also can be employed.

The methods of the invention also relate to administering to the respiratory tract of a subject, particles and/or compositions comprising the particles of the invention, which can be enclosed in a receptacle. As described herein, the invention is drawn to methods of delivering the particles of the invention, or the invention is drawn to methods of delivering respirable compositions comprising the particles of the invention. As used herein, the term "receptacle" includes but is not limited to, for example, a capsule, blister, film covered container well, chamber and other suitable means of storing particles, a powder or a respirable composition in an inhalation device known to those skilled in the art. Receptacles containing the pharmaceutical composition are stored 2-8° C.

The invention is also drawn to receptacles which are capsules, for example, capsules designated with a particular capsule size, such as 2, 1, 0, 00 or 000. Suitable capsules can be obtained, for example, from Shionogi (Rockville, Md.). Blisters can be obtained, for example, from Hueck Foils, (Wall, N.J.). Other receptacles and other volumes thereof suitable for use in the instant invention are known to those skilled in the art.

In a specific example, dry powder from a dry powder inhaler receptacle, e.g., capsule, holding 25 mg nominal powder dose having at 95% L-Dopa load, i.e., 23.75 mg L-Dopa, could be administered in a single breath. Based on a conservative 4-fold dose advantage, the 23.75 mg delivered in one breath would be the equivalent of about 95 mg of L-Dopa required in oral administration. Several such capsules can be employed to deliver higher doses of L-Dopa. For instance a size 4 capsule can be used to deliver 50 mg of L-Dopa to the pulmonary system to replace (considering the same conservative 4-fold dose advantage) a 200 mg oral dose.

The invention further is related to methods for administering to the pulmonary system a therapeutic dose of the medicament in a small number of steps, and preferably in a single, breath activated step. The invention also is related to methods of delivering a therapeutic dose of a drug to the pulmonary system, in a small number of breaths, and preferably in one or two single breaths. The methods includes administering particles from a receptacle having, holding, containing, storing or enclosing a mass of particles, to a subject's respiratory tract.

In one example, at least 80% of the mass of the particles stored in the inhaler receptacle is delivered to a subject's respiratory system in a single, breath-activated step. In another embodiment, at least 1 milligram of L-Dopa is delivered by administering, in a single breath, to a subject's respiratory tract particles enclosed in the receptacle. Preferably at least 10 milligrams of L-Dopa is delivered to a subject's respiratory tract. Amounts as high as 15, 20, 25, 30, 35, 40 and 50 milligrams can be delivered.

Delivery to the pulmonary system of particles in a single, breath-actuated step is enhanced by employing particles which are dispersed at relatively low energies, such as, for example, at energies typically supplied by a subject's inhalation. Such energies are referred to herein as "low." As used herein, "low energy administration" refers to administration wherein the energy applied to disperse and/or inhale the particles is in the range typically supplied by a subject during inhaling.

The invention also is related to methods for efficiently delivering powder particles to the pulmonary system. For example, but not limited to, at least about 70% or at least about 80% of the nominal powder dose is actually delivered. As used herein, the term "nominal powder dose" is the total amount of powder held in a receptacle, such as employed in an inhalation device. As used herein, the term nominal drug dose is the total amount of medicament contained in the nominal amount of powder. The nominal powder dose is related to the nominal drug dose by the load percent of drug in the powder.

Properties of the particles enable delivery to patients with highly compromised lungs where other particles prove ineffective for those lacking the capacity to strongly inhale, such as young patients, old patients, infirm patients, or patients with asthma or other breathing difficulties. Further, patients suffering from a combination of ailments may simply lack the ability to sufficiently inhale. Thus, using the methods and particles for the invention, even a weak inhalation is sufficient to deliver the desired dose. This is particularly important when using the particles of the instant invention as rescue therapy for a patient suffering from debilitating illness of Parkinson's disease.

Aerosol dosage, formulations and delivery systems may be selected for a particular therapeutic application, as described, for example, in Gonda, I. "Aerosols for delivery of therapeutic and diagnostic agents to the respiratory tract," in *Critical Reviews in Therapeutic Drug Carrier Systems,* 6: 273-313, 1990; and in Moren, "Aerosol dosage forms and formulations," in: *Aerosols in Medicine. Principles, Diagnosis and Therapy*, Moren, et al., Eds, Esevier, Amsterdam, 1985.

The method of the invention includes delivering to the pulmonary system an effective amount of a medicament such as, for example, a medicament described above. As used herein, the term "effective amount" means the amount needed to achieve the desired effect or efficacy. The actual effective amounts of drug can vary according to the specific drug or combination thereof being utilized, the particular composition formulated, the mode of administration, and the age, weight, condition of the patient, and severity of the episode being treated. In the case of a dopamine precursor, agonist or combination thereof it is an amount which reduces the Parkinson's symptoms which require therapy. Dosages for a particular patient are described herein and can be determined by one of ordinary skill in the art using conventional considerations, (e.g. by means of an appropriate, conventional pharmacological protocol). For example, effective amounts of oral L-Dopa range from about 50 milligrams (mg) to about 500 mg. In many instances, a common ongoing (oral) L-Dopa treatment schedule is 100 mg eight (8) times a day.

It has been discovered in this invention that pulmonary delivery of L-Dopa doses, when normalized for body weight, result in at least a 2-fold increase in plasma level as well as in therapeutical advantages in comparison with oral administration. Significantly higher plasma levels and therapeutic advantages are possible in comparison with oral administration. In one example, pulmonary delivery of L-Dopa results in a plasma level increase ranging from about 2-fold to about 10-fold when compared to oral administration. Plasma levels that approach or are similar to those obtained with intravenous administration can be obtained.

Assuming that bioavailability remains the same as dosage is increased, the amount of oral drug, e.g. L-Dopa, required to achieve plasma levels comparable to those resulting from pulmonary delivery by the methods of the invention can be determined at a given point after administration. In a specific example, the plasma levels 2 minutes after oral and administration by the methods of the invention, respectively, are 1 μg/ml L-Dopa and 5 μg/ml L-Dopa. Thus 5 times the oral dose would be needed to achieve the 5 μg/ml level obtained by administering the drug using the methods of the invention. In another example, the L-Dopa plasma levels at 120 minutes after administration are twice as high with the methods of the invention when compared to oral administration. Thus twice as much L-Dopa is required after administration 1 μg/ml following oral administration in comparison to the amount administered using the methods of the invention.

To obtain a given drug plasma concentration, at a given time after administration, less drug is required when the drug is delivered by the methods of the invention than when it is administered orally. Generally, at least a two-fold dose reduction can be employed in the methods of the invention in comparison to the dose used in conventional oral administration. A much higher dose reduction is possible. In one embodiment of the invention, a five fold reduction in dose is employed and reductions as high as about ten fold can be used in comparison to the oral dose.

At least a two-fold dose reduction also is employed in comparison to other routes of administration, other than intravenous, such as, for example, intramuscular, subcutaneous, buccal, nasal, intra-peritoneal, rectal.

In addition or alternatively to the pharmacokinetic effect, (e.g., serum level, dose advantage) described above, the dose advantage resulting from the pulmonary delivery of a drug, e.g., L-Dopa, used to treat Parkinson's disease, also can be described in terms of a pharmacodynamic response. Compared to the oral route, the methods of the invention avoid inconsistent medicament uptake by intestines, avoidance of delayed uptake following eating, avoidance of first pass catabolism of the drug in the circulation and rapid delivery from lung to brain via aortic artery.

Preferably, the effective amount is delivered on the "first pass" of the blood to the site of action. The "first pass" is the first time the blood carries the drug to and within the target organ from the point at which the drug passes from the lung to the vascular system. Generally, L-Dopa is released in the blood stream and delivered to its site of action within a time period which is sufficiently short to provide therapy to the patient being treated. In many cases, L-Dopa can reach the central nervous system in less than about 10 minutes, often as quickly as two minutes and even faster.

Preferably, the patient's symptoms abate within minutes and generally no later than one hour. In one embodiment of the invention, the release kinetics of the medicament are substantially similar to the drug's kinetics achieved via the intravenous route. In another embodiment of the invention, the $T_{max}$ of L-Dopa in the blood stream ranges from about 1 to about 10 minutes. As used herein, the term $T_{max}$ means the point at which levels reach a maximum concentration. In many cases, the onset of treatment obtained by using the methods of the invention is at least two times faster than onset of treatment obtained with oral delivery. Significantly faster treatment onset can be obtained. In one example, treatment onset is from about 2 to about 10 times faster than that observed with oral administration.

Particles and methods for delivering L-Dopa to the pulmonary system are described in U.S. patent application Ser. No. 09/665,252 entitled "Pulmonary Delivery In Treating Disorders of the Central Nervous System", filed on Sep. 19, 2000, now U.S. Pat. No. 6,514,482 issued on Jan. 4, 2003, and U.S.

patent application Ser. No. 09/877,734 entitled "Pulmonary Delivery In Treating Disorders of the Central Nervous System", filed, Jun. 8, 2001; the contents of both is incorporated herein by reference in their entirety.

If desired, particles which have fast release kinetics, suitable in rescue therapy, can be combined with particles having sustained release, suitable in treating the chronic aspects of a condition. For example, in the case of Parkinson's disease, particles designed to provide rescue therapy can be co-administered with particles having controlled release properties.

The administration of more than one dopamine precursor, agonist or combination thereof, in particular L-Dopa, carbidopa, apomorphine, and other drugs can be provided, either simultaneously or sequentially in time. Carbidopa, for example, is often administered to ensure that peripheral carboxylase activity is completely shut down. Intramuscular, subcutaneous, oral and other administration routes can be employed. In one embodiment, these other agents are delivered to the pulmonary system. These compounds or compositions can be administered before, after or at the same time. In a preferred embodiment, particles that are administered to the respiratory tract include both L-Dopa and carbidopa. The term "co-administration" is used herein to mean that the specific dopamine precursor, agonist or combination thereof and/or other compositions are administered at times to treat the episodes, as well as the underlying conditions described herein.

In one embodiment chronic L-Dopa therapy includes pulmonary delivery of L-Dopa combined with oral carbidopa. In another embodiment, pulmonary delivery of L-Dopa is provided during the episode, while chronic treatment can employ conventional oral administration of L-Dopa/carbidopa.

The present invention will be further understood by reference to the following non-limiting examples.

EXEMPLIFICATIONS

Preparation of Dry Particles Containing L-Dopa

Example 1

Particles Comprising L-Dopa and Trehalose

Particles with a formulation containing L-Dopa and trehalose were prepared as follows: The aqueous solution was formed by adding 2.375 g L-Dopa and 125 mg trehalose to 700 ml of USP water. The organic solution comprised 300 ml of ethanol. The aqueous solution and the organic solution were combined in a static mixer. A 1 L total combination volume was used, with a total solute concentration of 2.5 g/L in 30/70 ethanol/water. The combined solution flowed from the static mixer into a 2 fluid atomizer and the resulting atomized droplets were spray dried under the following process conditions:

| | |
|---|---|
| Inlet temperature | ~135° C. |
| Outlet temperature from the drying drum | ~49 to 53° C. |
| Nitrogen drying gas = | 95 kg/hr |
| Atomization rate = | 14 g/min |
| 2 Fluid internal mixing nozzle atomizer | |
| Liquid feed rate = | 70 ml/min |
| Pressure in drying chamber = | −2.0 in water |

The resulting particles had a FPF(5.6) of 33%, and a FPF (3.4) of 12%, both measured using a 2-stage ACI.

The combination solution flowing out of the static mixer was fed into a rotary atomizer. The contact between the atomized droplets from the atomizer and the heated nitrogen caused the liquid to evaporate from the droplets, resulting in dry porous particles. The resulting gas-solid stream was fed to bag filter that retained the resulting dry particles, and allowed the hot gas stream containing the drying gas (nitrogen), evaporated water, and ethanol to pass. The dry particles were collected into a product collection vessel.

In order to obtain dry particles of particular physical and chemical characteristics, in vitro characterization tests can be carried out on the finished dry particles, and the process parameters adjusted accordingly, as described above. Particles containing 95 wt % L-Dopa and 5 wt % trehalose were produced using this method. In this manner, the desired aerodynamic diameter, geometric diameter, and particle density could be obtained for these particles in real-time, during the production process.

Example 2

Particles Comprising L-Dopa, Trehalose and Sodium Chloride

Particles with a formulation containing L-Dopa, trehalose and sodium chloride were prepared as follows: The aqueous solution was formed by adding 2.325 g L-Dopa, 125 mg trehalose and 50 mg sodium chloride to 700 ml of USP water. The organic solution comprised 300 ml of ethanol. The aqueous solution and the organic solution were combined in a static mixer. A 1 L total combination volume was used, with a total solute concentration of 2.5 g/L in 30/70 ethanol/water. The combined solution flowed from the static mixer into a 2 fluid atomizer and the resulting atomized droplets were spray dried under the following process conditions:

| | |
|---|---|
| Inlet temperature | ~135° C. |
| Outlet temperature from the drying drum | ~49 to 53° C. |
| Nitrogen drying gas = | 95 kg/hr |
| Atomization rate = | 14 g/min |
| 2 Fluid internal mixing nozzle atomizer | |
| Liquid feed rate = | 70 ml/min |
| Liquid feed temperature | ~50° C. |
| Pressure in drying chamber = | −2.0 in water |

The resulting particles had a FPF(5.6) of 59%, and a FPF (3.4) of 40%, both measured using a 2-stage ACI. The volume mean geometric diameter was 17 μm at 1.0 bar.

The combination solution flowing out of the static mixer was fed into a 2-fluid atomizer. The contact between the atomized droplets from the atomizer and the heated nitrogen caused the liquid to evaporate from the droplets, resulting in dry porous particles. The resulting gas-solid stream was fed to bag filter that retained the resulting dry particles, and allowed the hot gas stream containing the drying gas (nitrogen), evaporated water, and ethanol to pass. The dry particles were collected into a product collection vessel.

In order to obtain dry particles of particular physical and chemical characteristics, in vitro characterization tests can be carried out on the finished dry particles, and the process parameters adjusted accordingly, as described above. Particles containing 93 wt % L-Dopa, 5 wt % trehalose and 2 wt % sodium chloride produced using this method had a VMGD of 17 μm measured by Rodos at 1 bar and a VMGD of 12 μm at 2 bar, FPF(5.6) of 59%. In this manner, the desired aerodynamic diameter, geometric diameter, and particle density could be obtained for these particles in real-time, during the production process.

Example 3

Particles Comprising L-Dopa and DPPC

Particles with a formulation containing L-Dopa and DPPC were prepared as follows: The aqueous solution was formed by adding 1.1875 g L-Dopa to 300 ml of USP water. The organic solution comprised 62.5 mg DPPC in 700 ml of ethanol. The aqueous solution and the organic solution were combined in a static mixer. A 1 L total combination volume was used, with a total solute concentration of 1.25 g/L in 70/30 ethanol/water. The combined solution flowed from the static mixer into a 2 fluid atomizer and the resulting atomized droplets were spray dried under the following process conditions:

| | |
|---|---|
| Inlet temperature | ~108° C. |
| Outlet temperature from the drying drum | ~49 to 53° C. |
| Nitrogen drying gas = | 95 kg/hr |
| Atomization rate = | 18 g/min |
| 2 Fluid internal mixing nozzle atomizer | |
| Liquid feed rate = | 70 ml/min |
| Liquid feed temperature | ~50° C. |
| Pressure in drying chamber = | −2.0 in water |

The resulting particles had a FPF(5.6) of 29%, and a FPF (3.4) of 10%, both measured using a 2-stage ACI. The volumetric mean geometric diameter was 7.9 µm at 1 bar.

The combination solution flowing out of the static mixer was fed into a rotary atomizer. The contact between the atomized droplets from the atomizer and the heated nitrogen caused the liquid to evaporate from the droplets, resulting in dry porous particles. The resulting gas-solid stream was fed to bag filter that retained the resulting dry particles, and allowed the hot gas stream containing the drying gas (nitrogen), evaporated water, and ethanol to pass. The dry particles were collected into a product collection vessel.

In order to obtain dry particles of particular physical and chemical characteristics, in vitro characterization tests can be carried out on the finished dry particles, and the process parameters adjusted accordingly, as described above. Particles containing 95 wt % L-Dopa and 5 wt % DPPC were produced using this method. In this manner, the desired aerodynamic diameter, geometric diameter, and particle density could be obtained for these particles in real-time, during the production process.

Example 4

Particles Comprising L-Dopa, DPPC and Sodium Chloride

Particles with a formulation containing L-Dopa, DPPC and sodium chloride were prepared as follows: The aqueous solution was formed by adding 1.125 g L-Dopa and 25 mg sodium chloride to 300 ml of USP water. The organic solution comprised 100 mg DPPC in 700 ml of ethanol. The aqueous solution and the organic solution were combined in a static mixer. A 1 L total combination volume was used, with a total solute concentration of 1.25 g/L in 70/30 ethanol/water. The combined solution flowed from the static mixer into a 2 fluid atomizer and the resulting atomized droplets were spray dried under the following process conditions:

| | |
|---|---|
| Inlet temperature | ~108° C. |
| Outlet temperature from the drying drum | ~49 to 53° C. |
| Nitrogen drying gas = | 95 kg/hr |
| Atomization rate = | 18 g/min |
| 2 Fluid internal mixing nozzle atomizer | |
| Liquid feed rate = | 70 ml/min |
| Liquid feed temperature | ~50° C. |
| Pressure in drying chamber = | −2.0 in water |

The resulting particles had a FPF(5.6) of 70%, and a FPF (3.4) of 40%, both measured using a 2-stage ACI. The volume mean geometric diameter was 14 µm at 1.0 bar.

The combination solution flowing out of the static mixer was fed into a rotary atomizer. The contact between the atomized droplets from the atomizer and the heated nitrogen caused the liquid to evaporate from the droplets, resulting in dry porous particles. The resulting gas-solid stream was fed to bag filter that retained the resulting dry particles, and allowed the hot gas stream containing the drying gas (nitrogen), evaporated water, and ethanol to pass. The dry particles were collected into a product collection vessel.

In order to obtain dry particles of particular physical and chemical characteristics, in vitro characterization tests can be carried out on the finished dry particles, and the process parameters adjusted accordingly, as described above. Particles containing 90 wt % L-Dopa, 8 wt % DPPC and 2 wt % sodium chloride produced using this method had a VMGD of 14 µm measured by Rodos at 1 bar and a VMGD of 11 µm at 2 bar, FPF(5.6) of 70%. In this manner, the desired aerodynamic diameter, geometric diameter, and particle density could be obtained for these particles in real-time, during the production process.

What is claimed is:

1. A method of treating a patient with Parkinson's disease, that comprises:
    administering to the respiratory tract of the patient particles that include about 90 weight percent or more levodopa, and a salt wherein the formulation contains less than 10% by weight of a salt, and a non-reducing sugar,
wherein the particles are delivered to the pulmonary system.

2. A method of treating a patient with Parkinson's disease, that comprises:
    administering to the respiratory tract of the patient particles that consist essentially of about 90 weight percent or more levodopa, a non-reducing sugar and a salt wherein the formulation contains less than 10% by weight of the salt,
wherein the particles are delivered to the pulmonary system and have a tap density about 0.4 g/cm$^3$ or less, a volume median geometric diameter about 5 micrometers or more, and an aerodynamic diameter of from about 1 micrometer to about 5 micrometers.

3. The method of claim 2, wherein the particles have an aerodynamic diameter of from about 1 micrometer to about 3 micrometers.

4. The method of claim 2, wherein the particles have an aerodynamic diameter of from about 3 micrometer to about 5 micrometers.

5. The method of claim 2, wherein the particles gave a tap density about 0.3 g/cm$^3$ or less.

6. The method of claim 2, wherein the particles gave a tap density about 0.2 g/cm$^3$ or less.

7. The method of claim 2, wherein the particles gave a tap density about 0.1 g/cm$^3$ or less.

8. A method of treating a patient with Parkinson's disease, that comprises:
   administering to the respiratory tract of the patient particles that include about 90 weight percent or more levodopa, NaCl in an amount less than 10% by weight of NaCl, and a non-reducing sugar,
wherein the particles are delivered to the pulmonary system.

9. The method of claim 8, wherein the non-reducing sugar is trehalose.

10. A method of delivering an effective amount of L-Dopa to the pulmonary system, comprising:
    providing a mass of particles that include, by weight, about 90 percent or more L-Dopa, about 10 percent or less trehalose, and sodium chloride wherein the formulation contains about 3 percent or less sodium chloride; and
    administering via simultaneous dispersion and inhalation the particles, from a receptacle having the mass of the particles, to a human subject's respiratory tract.

* * * * *